United States Patent [19]
Alburn et al.

[11] 3,932,391
[45] Jan. 13, 1976

[54] CEPHALOSPORIN ISOCYANATES

[75] Inventors: Harvey E. Alburn, West Chester; William Dvonch, Radnor, both of Pa.

[73] Assignee: American Home Products Corporation, New York, N.Y.

[22] Filed: Oct. 2, 1972

[21] Appl. No.: 294,411

[52] U.S. Cl............ 260/243 C; 260/239.1; 424/246; 424/271
[51] Int. Cl.²........................................ C07D 501/20
[58] Field of Search................................ 260/243 C

[56] References Cited
UNITED STATES PATENTS

| | | | |
|---|---|---|---|
| 3,673,183 | 6/1972 | Erickson | 260/243 C |
| 3,708,479 | 1/1973 | Welch et al. | 260/243 C |
| 3,763,154 | 10/1973 | Henniger | 260/243 C |

*Primary Examiner*—Nicholas S. Rizzo
*Assistant Examiner*—Mary C. Vaughn
*Attorney, Agent, or Firm*—Stephen Venetianer

[57] ABSTRACT

Novel penicillin and cephalosporin isocyanates are described which are useful intermediates for reaction with compounds containing an active hydrogen to produce penicillin and cephalosporin derivatives having activity against gram positive and/or gram negative bacteria.

18 Claims, No Drawings

CEPHALOSPORIN ISOCYANATES

This invention relates to novel penicillin and cephalosporin isocyanates, processes for their preparation and use of such isocyanates to prepare penicillins and cephalosporins having activity against gram positive and/or gram negative bacteria.

Accordingly, one aspect of the present invention relates to novel penicillin and cephalosporin isocyanates.

Another aspect of the present invention relates to the use of amino substituted penicillins or cephalosporins to manufacture the novel isocyanates of the present invention.

A further aspect of the present invention relates to the isocyanates of the present invention as intermediates in the synthesis of penicillins and cephalosporins having antibacterial activity.

These and other aspects of the present invention will be apparent from the following description.

In its broadest aspects the present invention relates to isocyanates of the formulae:

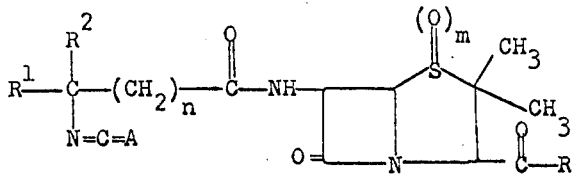

I and

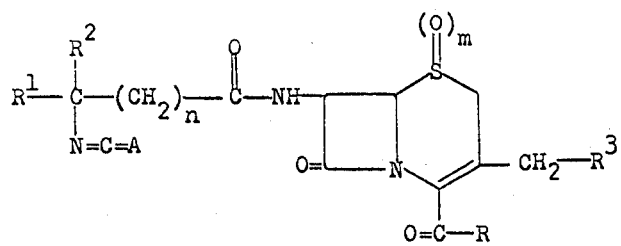

II wherein:

A is a member selected from the group consisting of oxygen and sulfur;

R is an organic radical;

$R^1$ and $R^2$ are selected from the group consisting of hydrogen, lower alkyl, alicyclic, aryl, aryl(lower)alkyl, heterocyclic, heterocyclic lower alkyl or any other organic radicals described in the penicillin or cephalosporin literature linked directly or through

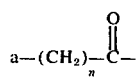

radical to the amino group at the 6-position of a semi-synthetic penicillin or at the 7-position of a semi-synthetic cephalosporin. Any of the foregoing radicals may contain one or more substituents as identified hereinafter;

$R^1$ and $R^2$ may be joined together to form an alicyclic or heterocyclic ring;

$R^3$ may be any organic substituent that is considered suitable in the cephalosporin art for substitution at the 3-position on the cephalosporin nucleus by linkage through the methylene radical and $n$ is a number from 0 through 3; $m$ is a number which is either 0 or 1.

Heterocyclic as defined by $R^1$ and $R^2$ is preferably a mono heterocyclic ring of aromatic character having five to six ring atoms in the heterocyclic ring and up to and including three hetero atoms selected from the class consisting of oxygen, sulfur and nitrogen. The heterocyclic ring may have a fused-on benzene ring attached thereto.

The term "aryl" as used throughout the specification means a mono or bicyclic carbocyclic ring of aromatic character which may or may not be substituted. The term "alicyclic" as used throughout the specification means a mono or bicyclic carbocyclic ring of non-aromatic character having four to 10 carbon atoms and which is either completely saturated, contains a single double bond or two or three conjugated or non-conjugated double bonds as represented by cycloalkyl, cycloalkenyl, cycloalkadienyl or cycloalkatrienyl.

The word "substituted" as used throughout the specification means a radical substituted with a group selected from the class consisting of nitro, halogen, trifluoromethyl, (lower)alkoxy, (lower)alkyl, amino, hydroxy, sulfamyl, di(lower)alkylamino and (lower)alkanoylamino. The symbol "$\phi$" means phenyl.

The term (lower)alkyl, except where otherwise indicated, means a straight or branched chain having one through six carbon atoms (e.g. methyl, ethyl, isopropyl, hexyl, tert-butyl, etc.) The term "halogen" means chlorine, fluorine, bromine and iodine. The term (lower)alkoxy means a straight or branched chain having one through six carbon atoms (e.g. methoxy, ethoxy, propoxy, etc.)

In formulas I and II, those groups represented by R are selected from the class consisting of

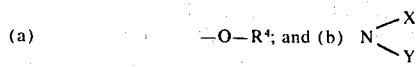

wherein: $R^4$ is a member selected from the class consisting of (1) hydrogen; (2) a metallic cation such as sodium, potassium, calcium, aluminum, etc.; (3) a non-metallic cation formed from a trialkylamine or a dialkylamine (e.g. triethylamine, procaine, dibenzylamine, N,N'-dibenzylethylene diamine, 1-ephenamine); (4) N-(lower)alkyl piperidines (e.g. N-methylpiperidine); (5) a heterocyclic quaternary ammonium group (e.g. pyridinium, quinolinium, picolinium); (6) other non-toxic amines that will form salts with the carboxyl group; (7) an organic group which is capable of smooth reaction with the carboxylic acid group to form an ester and is stable during reaction of a compound of formulae I and II with a compound containing an active hydrogen and such organic groups being removable chemically or enzymatically under mild conditions without destruction of the penicillin or cephalosporin nucleus; and (8) $R^4$ and $R^3$ may be joined together to form a lactone when $R^3$ is hydroxyl.

Illustrative of organic radicals represented by $R^4$ are aryl, aryl(lower)alkylene, cycloalkyl, substituted aryl(lower) alkylene, halo(lower)alkyl, $C_3$–$C_7$ tert(lower)alkyl, aroyl—$CH_2$—, substituted aroyl—$CH_2$—, diarylmethylene, substituted diarylmethylene, phthalimido(lower)alkylene, succinimido(lower)alkylene, $C_5$ to $C_7$ tert-alkenyl, $C_5$ to $C_7$ tert-alkynyl as well as the following groups:

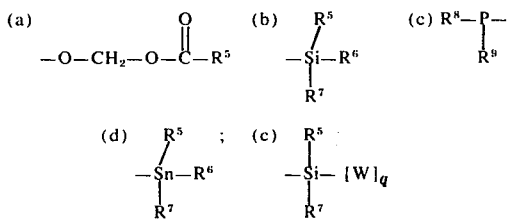

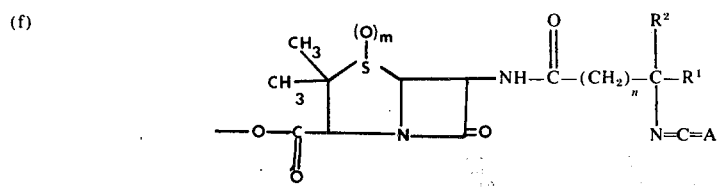

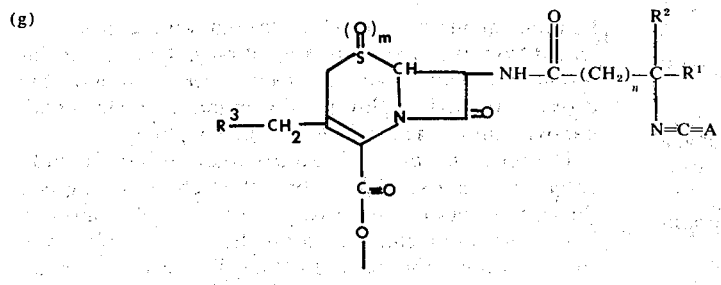

wherein:
  $q$ is a number which is either 0 or 1;
  $R^5$, $R^6$ and $R^7$ are selected from the class consisting of lower alkyl, aryl(lower)alkyl, cycloalkyl of 5 to 8 carbon atoms and aryl; $R^8$ and $R^9$ are each selected from the class consisting of: aryloxy, (lower)alkoxy, arylthio, aryl(lower)alkyloxy, (lower)alkyl, aryl, halo(lower)alkyl, aryl(lower)alkyl and W; and $R^8$ and $R^9$ may be joined together to form with phosphorus, the ring

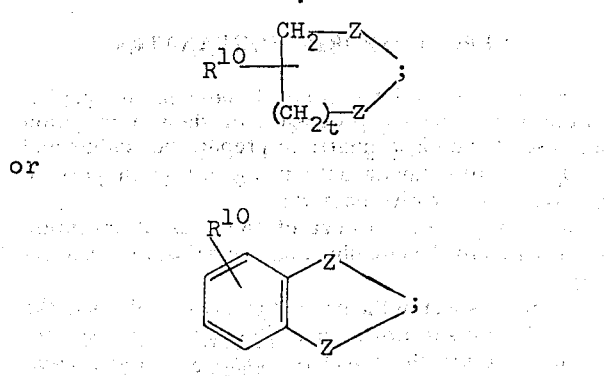

wherein Z is selected from the class consisting of oxygen, $CH_2$ and sulfur; $R^{10}$ is hydrogen or (lower)alkyl; t is an integer from 1 to 6; W is selected from the group consisting of halogen, and a group represented by formulas (f) or (g) supra.

Examples of suitable radicals described in the prior art represented by $R^4$ are found in the following U.S. Pat. Nos., among others, the disclosures of which are incorporated herein by reference: 3,249,622; 3,284,451; 3,466,275; 3,483,188; 3,485,819; 3,553,203; 3,558,602; 3,574,799; 3,621,011; 3,635,953; 3,654,266; 3,655,658; 3,660,395. Applicants also incorporate herein by reference the disclosure of copending application, Ser. Nos. 186,397, 197,142 and 217,942.

X and Y in the formula

when taken separately are both electron withdrawing groups and when taken together with the nitrogen atom to which they are attached complete a cyclic electron withdrawing group. The electron withdrawing groups represented by X and Y alone or taken together are those defined in claim 8 and column 2, lines 58–66, and column 3, lines 1 through 75, of U.S. Pat. No. 3,635,953, the disclosure of which is incorporated herein as though fully described at this point. The preferred compounds represented by

are those of the formula

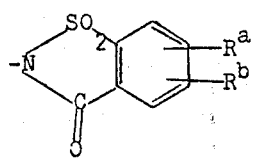

wherein $R^a$ and $R^b$ are selected from the class consisting of hydrogen, (lower)alkyl, (lower)alkoxy and halogen, preferably $R^a$ and $R^b$ are each hydrogen.

Illustrative of heterocyclic lower alkyl or heterocyclic radicals represented by $R^1$ and $R^2$ are thienyl, furyl, pyridyl, picolyl, pyrryl, thenyl, furfuryl, thianaphthenyl, benzothienyl, benzofuryl, isothiazolyl, indolyl, imidazolyl, oxazolyl, 1,2,4-triazolyl, 1,3,4-thiadiazolyl, 1,3,4-oxadiazinyl, 1,3,4-dithiazolyl, pyrimidinyl, benzimidazolyl, etc. Illustrative of aryl and aryl (lower)alkyl radicals represented by $R^1$ and $R^2$ are phenyl, benzyl, phenethyl, p-chlorophenyl, p-nitrophenyl, o-aminophenyl, p-hydroxyphenyl, naphthyl, tetrahydronaphthyl, m-trifluoromethylphenyl, etc. Alicyclic radicals represented by $R^1$ and $R^2$ alone or joined together are cyclobutyl, cyclopentyl, cyclohexyl, cyclooctyl, cyclopentenyl, cyclohexenyl, 1,4-cyclohexadienyl, cycloheptatrienyl, etc. Specific groups illustrated by $R^1$ and $R^2$ are found in U.S. Pat. Nos. 3,579,506; 3,531,470; 3,594,366; 3,483,188; 3,558,601; 3,595,855; 3,202,654; 3,268,514; 3,560,489; 3,579,514; 3,592,812; 3,518,260 and 3,627,761.

The term "aroyl" includes both monocyclic and bicyclic aromatic radicals having six through 10 ring carbon atoms as well as a monoheterocyclic radical as previously defined of aromatic character. Illustrative are nicotinoyl, isonicotinoyl, benzoyl, p-nitrobenzoyl, o-methylbenozyl, thenoyl, furoyl, napthoyl, etc.

Organic radicals defined by $R^3$ are selected from those known in the art as represented by the class consisting of hydrogen, hydroxy, a hydroxy group which is esterified with a carboxylic acid and in which the ester oxygens may be replaced by sulfur atoms, a quaternary ammonium group, a primary, secondary or tertiary amine [e.g. (lower)alkylamino, di(lower)alkylamino, phenyl (lower)alkylamino, N-heterocyclic tertiary amine, etc.], an azide group, a guanylmercapto group, an α-iminoalkylmercapto group and a mercapto group which has been etherified. Illustrative groups defined by $R^3$ may be found in U.S. Pat. Nos. 3,483,197; 3,553,203; 3,536,698; 3,627,760; 3,637,678; 3,641,021; and 3,644,347, the disclosures of which are incorporated herein by reference.

A more preferred class of compounds within the scope of the present invention nare represented by the formulae:

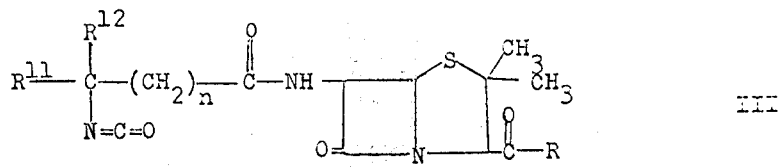

III

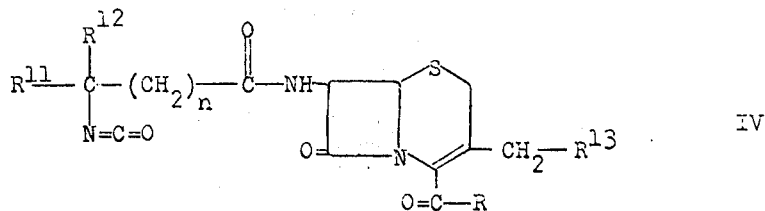

IV wherein:

R is selected from the group consisting of (a) $-O-R^4$ and (b)

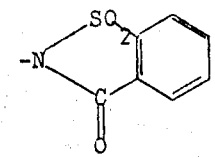

$R^{11}$ is selected from the class consisting of aryl and substituted aryl; cycloalkyl having four to eight ring atoms; cycloalkenyl having four to eight ring atoms; an alicyclic radical having six to eight carbon atoms and containing two or three conjugated or non-conjugated double bonds; a five or six membered heterocyclic ring of aromatic character having a single hetero atom selected from the class consisting of oxygen, sulfur and nitrogen;

$R^{12}$ is selected from the class consisting of hydrogen and lower alkyl;

$R^{13}$ is selected from the class consisting of hydrogen, a quaternary ammonium radical and an acyloxy radical derived from a hydrocarbon carboxylic acid having up to eight carbon atoms (e.g. acetoxy, propionoyloxy, butanolyloxy, pentanolyoxy, etc.)

The preferred compounds are those of formula III and IV wherein:

$R^4$ is selected from the class consisting of trimethylsilyl, 1,3,2-dioxaphospholanyl, tert-butyl, benzyl, phthalimidomethyl, succinimidomethyl, pivaloyloxymethyl, 2,2,2-trichloroethyl, trityl, dimethyl silene ester as described in U.S. Pat. No. 3,654,266, phenacyl and benzhydryl.

$R^{11}$ is selected from the class consisting of phenyl, substituted phenyl, cyclohexyl, 1,4-cyclohexadienyl, cyclohexenyl, thienyl; $R^{12}$ is hydrogen; and $R^{13}$ is selected from the class consisting of hydrogen, acetoxy and pyridinium; and n is 0.

The novel penicillin and cephalosporin isocyanate intermediates of the present invention may be prepared in accordance with the following reaction sequence:

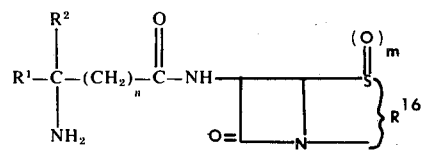

phosgene or thiophosgene

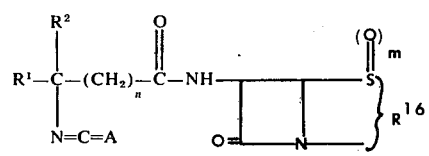

wherein $R^{16}$ may be either:

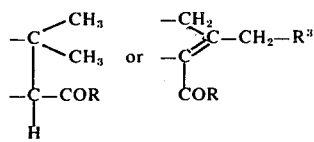

The foregoing reaction is preferably carried out in an inert anhydrous organic solvent at a temperature below −20°C. and preferably between about −25°C. and about −50°C. As solvents, toluene, dichlormethane, chloroform, ethylene dichloride and benzene may be employed. To facilitate the reaction, an organic base can be added to the reaction mixture to bind the hydrogen chloride formed; tertiary amines such as triethylamine, N-ethylpiperidine are advantageously used for this purpose.

The starting materials of formula I can be prepared by procedures well known in the art such as by acylation of 6-APA, 7-ACA, 7-ADCA or derivatives thereof.

Typical preparation of such compounds are illustrated in U.S. Pat. Nos. 3,594,366; 3,558,602; 3,518,260; 3,595,855; 3,213,083; 3,481,922; 3,483,188; 3,531,470.

The isocyanates of this invention react with an organic compound containing an active hydrogen atom or a carbionoid reagent (e.g. a Grignard compound or organolithium compound) to form non-toxic penicillins and cephalosporins having activity against gram positive and/or gram negative bacteria. The classes of compounds are those that will react with the selected isocyanate compound under temperature and pH conditions that will not result in destruction of the penicillin or cephalosporin nucleus. Thus, the isocyanate penicillins and cephalosporins of formula I and II may be reacted with the following type of compounds:

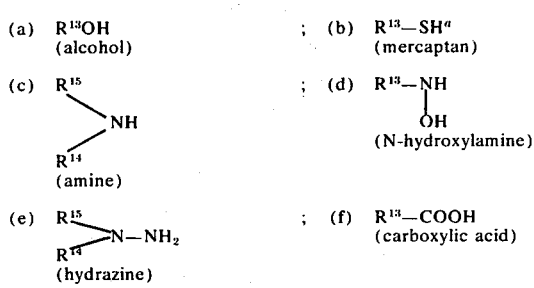

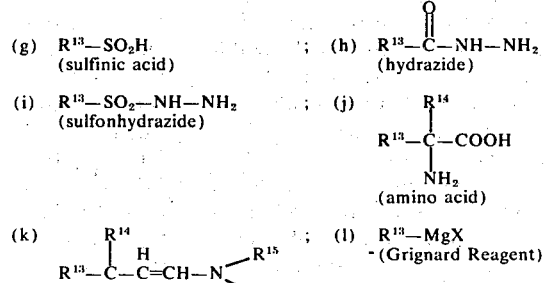

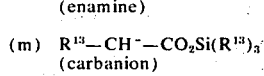

$R^{13}$ is selected from the class consisting of (lower)alkyl, aryl, ara(lower)alkyl, mono(lower)alkylamino(lower)alkyl, di(lower) alkylamino(lower)alkyl, cycloalkyl, halo(lower)alkyl; $R^{14}$ and $R^{15}$ are selected from the class consisting of hydrogen and $R^{13}$; $R^{14}$ and $R^{15}$ may be joined together to form with the nitrogen atom a five to seven member saturated heterocyclic ring which may contain one additional hetero atom selected from the class consisting of oxygen, sulfur and nitrogen.

The products obtained by reacting the isocyanates with an organic compound as defined in (a) through (m) supra have the following nucleus:

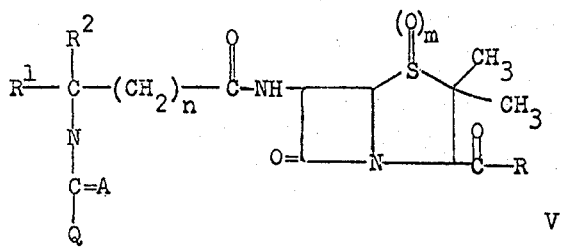

and

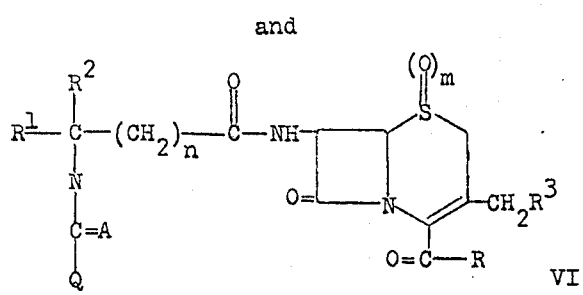

wherein Q is selected from the class consisting of:

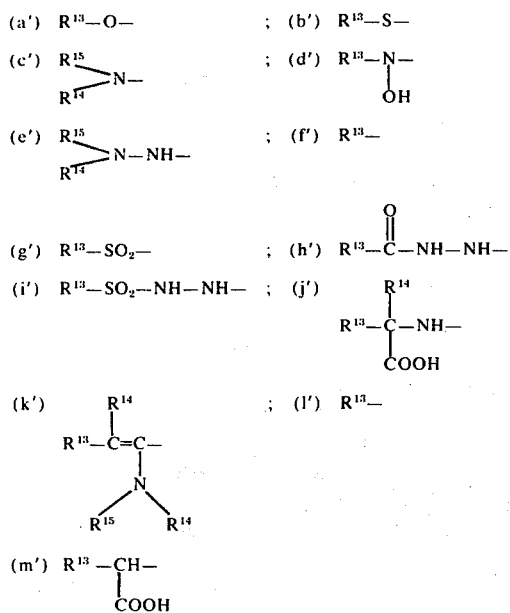

In reacting the isocyanates of the present invention with an active hydrogen containing compound of a carbionoid reagent as described supra, it is advantageous to use one or more catalysts. Suitable catalysts include inorganic bases such as sodium hydroxide or tertiary amines such as triethylamine, pyridine, N-methylmorpholine, triethylenediamine, N,N,N',N'-tetramethyl-1,3-diaminobutane, and N-methyl benzimidazole. Other catalysts that may be used are metal compounds such as di-n-butyltin diacetate, etc.

The conditions employed in reacting the isocyanates of the present invention with another compound to obtain a compound of formula V or VI must be such that there is no alteration or destruction of the penicillin or cephalosporin nucleus. Therefore, temperatures ranging from about −20°C. to about 45°C. and a pH of below about 10 should be used. The reaction is carried out preferably in the presence of an inert anhydrous organic solvent such as benzene, toluene, 1,2-dimethoxyethane, etc.

The penicillin or cephalosporin nucleus means the ring structure which has been identified in the art by the name "penam" and "cepham" (see U.S. Pat. No. 3,660,395, column 3).

The following examples are illustrative of the products and processes of the present invention:

EXAMPLE 1

6-[D-2-(1,4-cyclohexadien-1-yl)-2-isocyanatoacetamido]penicillanic acid, trimethyl silyl ester In a 4-necked 500 ml. flask equipped with a stirrer, dropping funnel with a phosphorous pentoxide drying tube, a thermometer, and a gas inlet tube through which nitrogen is admitted, toluene (60 ml.) and dry dihydroampicillin (7.03 g.; 0.0200 mole) are placed. Triethylamine (6.26 ml.; 0.0452 mole) is added over 20 min. The funnel is flushed with a small amount of toluene and freshly distilled trimethylchlorosilane (7.20 ml.; 0.568 mole) is added dropwise. Stirring is continued for 2.5 hr. Toluene (30 ml.) is added and the temperature is lowered to −60°C. Triethylamine (2.58 ml.; 0.0186 mole) is added. Then phosgene (5.10 g.; 0.0516 mole; 20.4 ml. of a 25% solution in toluene) is added while the temperature of the reaction is not allowed to rise above −40°C. After complete addition of the phosgene, stirring is continued for 3.0 hr. The greater part of the residual phosgene is then removed by vacuum distillation at −40°C. into a vessel cooled with liquid nitrogen. The temperature is slowly brought to −20°C. to remove the remaining traces of phosgene, trimethylchlorosilane and triethylamine. The reaction mixture is then taken slowly to room temperature and dryness.

The solid is dispersed in toluene and the insoluble triethylamine hydrochloride filtered off. The filtrate is concentrated in vacuo to give the title product.

The trimethyl silyl protective group may be split off in accordance with the procedure described in U.S. Pat. No. 3,249,622.

Dihydroampicillin as used throughout the specification means 6-[D-2-amino-2-(1,4-cyclohexadien-1-yl)acetamido]penicillanic acid.

EXAMPLE 2

6-[D-2-isocyanato-2-phenylacetamido]penicillanic acid, trimethyl silyl ester

Following the same procedure as described in Example 1 and using the same quantity of each reagent except that dihydroampicillin is replaced by ampicillin, the above titled product is obtained.

EXAMPLE 3

7-[D-2-(1,4-cyclohexadien-1-yl)-2-isocyanatoacetamido-]cephalosporanic acid, trimethyl silyl ester D-2-amino-2-(1,4-cyclohexadien-1-yl)acetic acid (3.06 g., 0.020 mole) is dissolved in 2-N sodium hydroxide (10 ml.) and dioxane (30 ml.) and o-nitrophenylsulfenyl chloride (4.16 g., 0.022 mole) are added in portions over 20 min. while 2-N sodium hydroxide (12 ml.) is added dropwise with stirring. The reaction mixture is stirred an additional hr. and then poured into icewater (200 ml.). The mixture is filtered, the pH adjusted to 2.5 with 6-N sulfuric acid, and then extracted with ethyl acetate (5 × 100 ml.). The extract is washed with water, brine, dried with sodium sulfate, and concentrated to give a quantitative yield of D-2-(1,4-cyclohexadien-1-yl)-2-o-nitrosulfenylaminoacetic acid.

A mixture of the o-nitrosulfenyl derivative of D-2-amino-2-(1,4-cyclohexadien-1-yl)acetic acid (6.12 g., 0.020 mole) and triethylamine (2.76 ml., 0.020 mole) dissolved in dimethylformamide (80 ml.) is treated dropwise with ethylchloroformate (1.90 ml., 0.020 mole) in ether (5 ml.) at −10°C. with stirring. After 20 min., 7-aminocephalosporanic acid (6.8 g., 0.025 mole) dissolved in ice-water (50 ml.) with triethylamine (3.86 ml., 0.028 mole) is added. The mixture is stirred with no external cooling for 1.5 hr., poured into ice-water (200 ml.) and extracted with ether (3 × 100 ml.). The pH of the aqueous phase is adjusted from 7.2 to 3.0 with 6-N sulfuric acid. The mixture is extracted with ethyl acetate (5 × 100 ml.). The extract is washed with water and brine, dried over sodium sulfate, filtered, and concentrated in vacuo. The yield of the blocked cephalosporin is 5.5 g. (50%). This material is deblocked by dissolving in methyl alcohol (75 ml.) and treating with thioacetamide (7.5 g., 0.10 mole) and glacial acetic acid (25 ml.) for 15 min. The precipitated bis(o-nitro-phenyl) disulfide is filtered off and the filtrate diluted with water (200 ml.). The organic solvents are removed in vacuo, and the aqueous solution extracted with ethyl acetate until no further color is extracted. The aqueous layer is lyophilized, and the dry solid is washed free of thioacetamide with several portions of 1:1 ethyl alcohol:ether to yield a hydrate of 7-[D-2-amino-2-(1,4-cyclohexadien-1-yl)acetamido]-cephalosporanic acid. Dissolution in water, filtration and lyophilization gives a purer product. This product is dehydrated by placing it in methylene chloride followed by the addition of triethylamine to form the soluble triethylamine salt of 7-[D-2-amino-2-(1,4-cyclohexadien-1-yl)acetamido] cephalosporanic acid which is dried with a Linde 4A molecular sieve such as described in U.S. Pat. No. 3,381,001. The dried product is then treated in the same manner as described in Example 1 to obtain the above titled product.

EXAMPLE 4

6-[2-(1-isocyanatocyclohexyl)acetamido]penicillanic acid, trimethyl silyl ester

Following the procedure of Example 1, 7.1 grams of 6-[2-(1-aminocyclohexyl)acetamido]penicillanic acid is reacted with 5.10 grams phosgene for 18 hours to produce the above titled product.

The 6-[2-(1-aminocyclohexyl)acetamido]penicillanic acid starting material is prepared as follows:

6-Aminopenicillanic acid (4.7 g., 21.9 meq.) is suspended in water (600 ml.) at a pH of 5.0 and temperature of 4°C. To this suspension is added with vigorous stirring the N-carboxy anhydride of 1-aminocyclohexaneacetic acid (4 g., 21.9 meq.). The mixture is allowed to remain at 4°C. with stirring for 24 hours. The resulting clear solution is lyophilized to yield 7.7 g. of the compound, 6-[2-(1-aminocyclohexyl)acetamido]-penicillanic acid.

EXAMPLE 5

7-(D-2-isocyanato-2-phenylacetamido]-3-methyl-8-oxo-5-thia-1-azabicyclo[4.2.0]-oct-2-ene-2-carboxylic acid, trimethyl silyl ester Following the procedure of Example 1, 3.65 grams of cephalolexin monohydrate is reacted with 5.10 grams phosgene for 18 hours to yield the above titled product.

EXAMPLE 6

7-(D-2-isocyanato-2-phenylacetamido)cephalosporanic acid, trimethyl silyl ester

Following the procedure of Example 1, 2.95 grams of cephaloglycin dihydrate is reacted with 5.10 g. phosgene for 18 hours to yield the above titled product.

EXAMPLE 7

6-[(1-isocyanatocyclohexyl)carboxamido]penicillanic acid, trimethyl silyl ester

Following the procedure of Example 1, 6.82 grams of 6-[(1-aminocyclohexyl)carboxamido]penicillanic acid is reacted with 5.10 grams phosgene to yield the above titled product.

EXAMPLE 8

6-[D-2-(1,4-cyclohexadien-1-yl)-2-isothiocyanatoacetamido]penicillanic acid, trimethyl silyl ester The above identified compound is prepared in the same manner as described in Example 1, using the same materials except that the phosgene is replaced by thiophosgene and the reaction time is 18 hours rather than 3 hours.

In each of Examples 4 through 8 the carboxyl protective group is removed by hydrolysis with water in accordance with prior art procedures such as described in U.S. Pat. No. 3,249,622.

EXAMPLE 9

In accordance with the procedure of Example 1, the following isocyanate penicillins can be obtained by reacting the appropriate α-amino substituted penicillin with phosgene or thiophosgene.

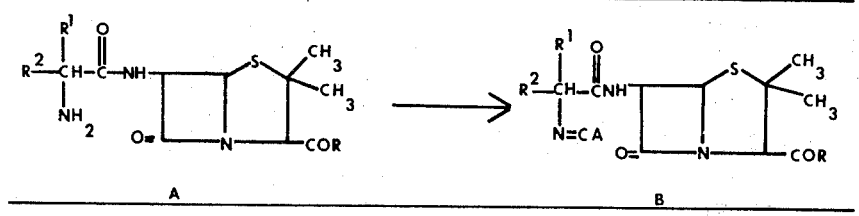
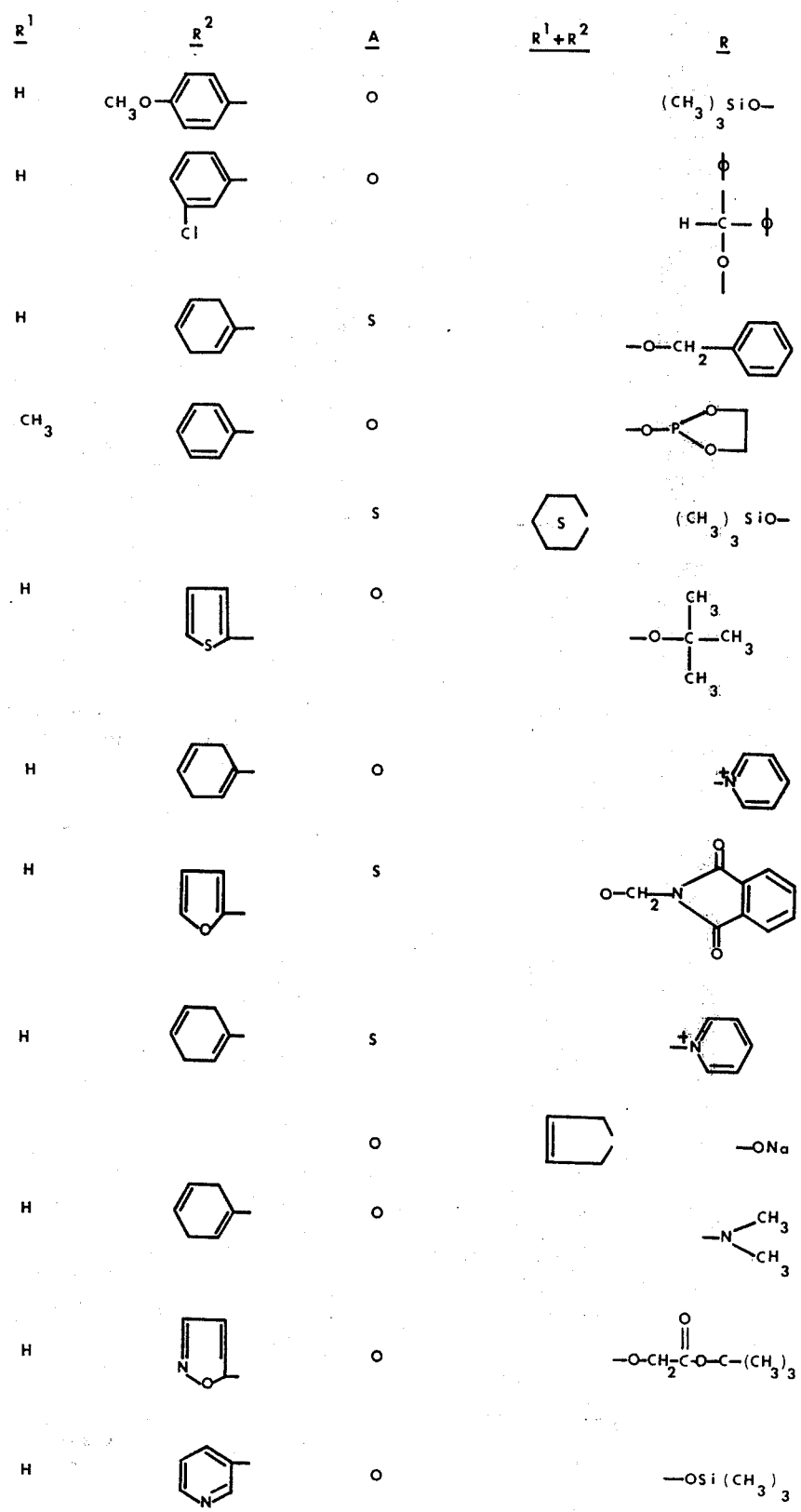

| $R^1$ | $R^2$ | $A$ | $R^1+R^2$ | $R$ |
|---|---|---|---|---|
| H | 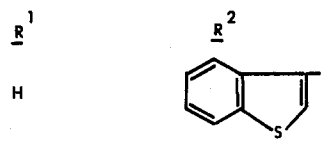 | O | | 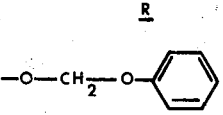 |
| H |  | O | | 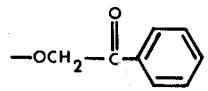 |
| H |  | O | | 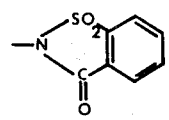 |
| H |  | O | | 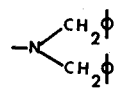 |
| H | | O | 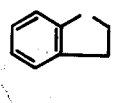 |  |
| $C_2H_5$ |  | O | | $-NH-SO_2-CH_3$ |
EXAMPLE 10
In accordance with the procedure of Example 1, the following isocyanate penicillins can be obtained by selecting the appropriate silene esters of α-amino substituted penicillins. The silenated esters are prepared as described in U.S. Pat. No. 3,654,266.
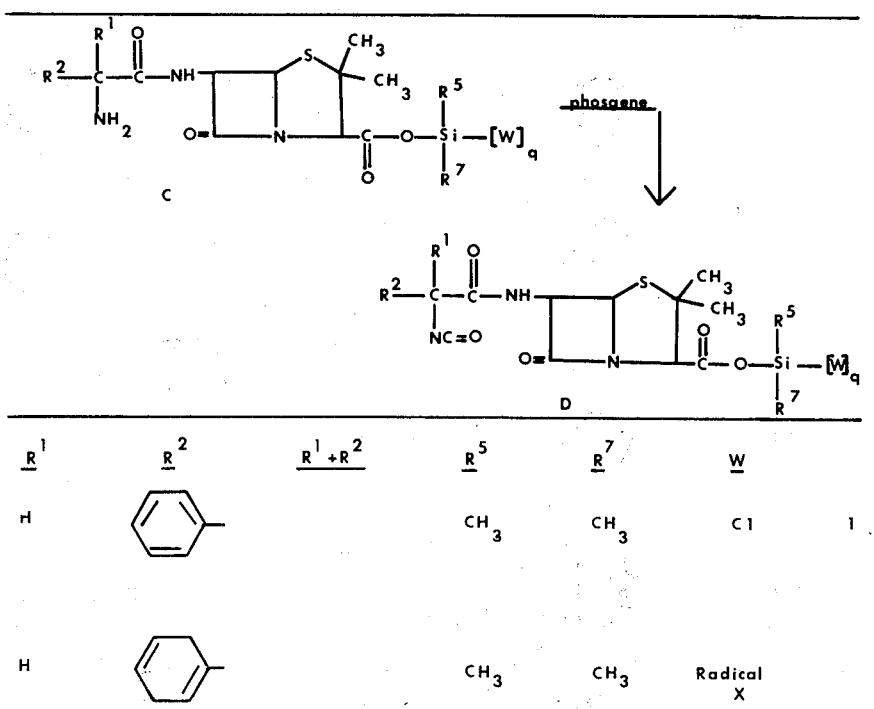

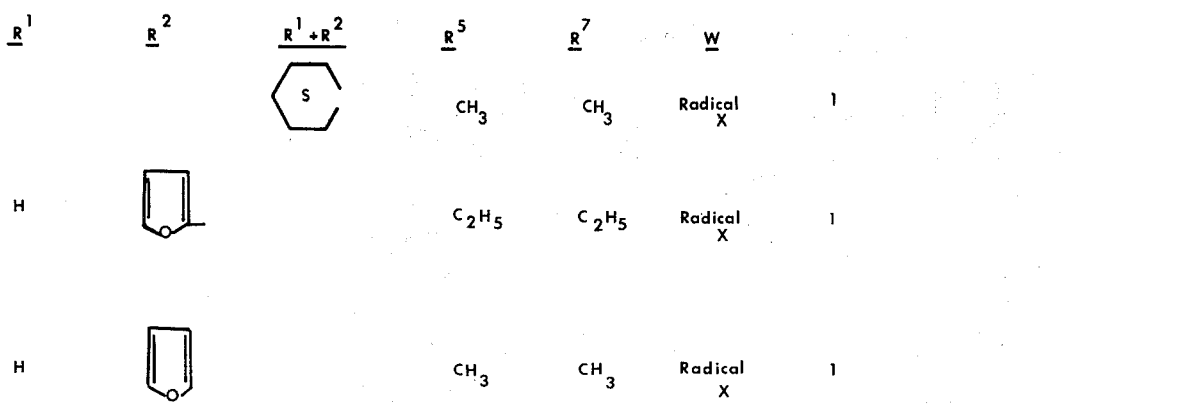
In this example, Radical X stands for:
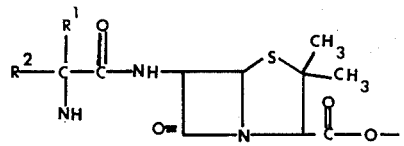
in formula C and the corresponding isocyanate in formula D.
EXAMPLE 11
In accordance with the procedure of Example 1, the following isocyanate cephalosporins can be obtained by reacting phosgene or thiophosgene with the appropriate α-amino substituted cephalosporin.
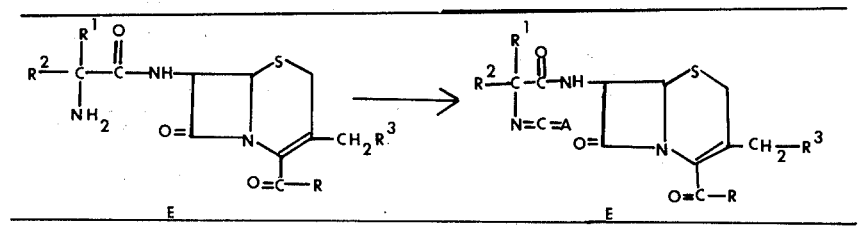
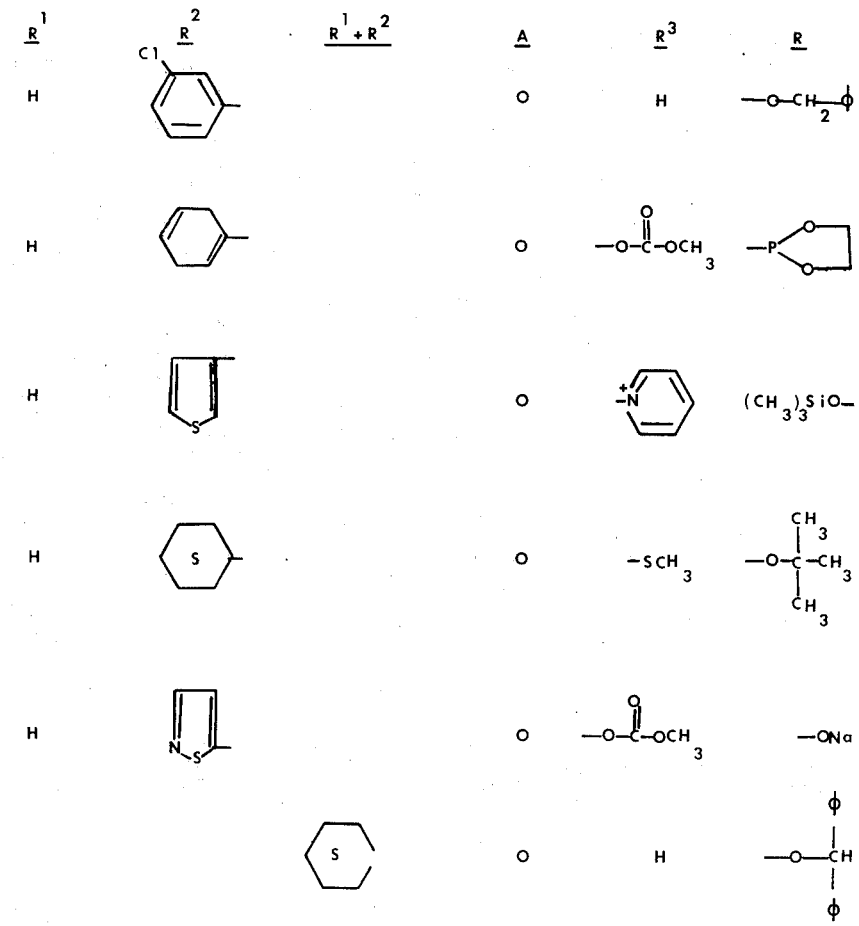

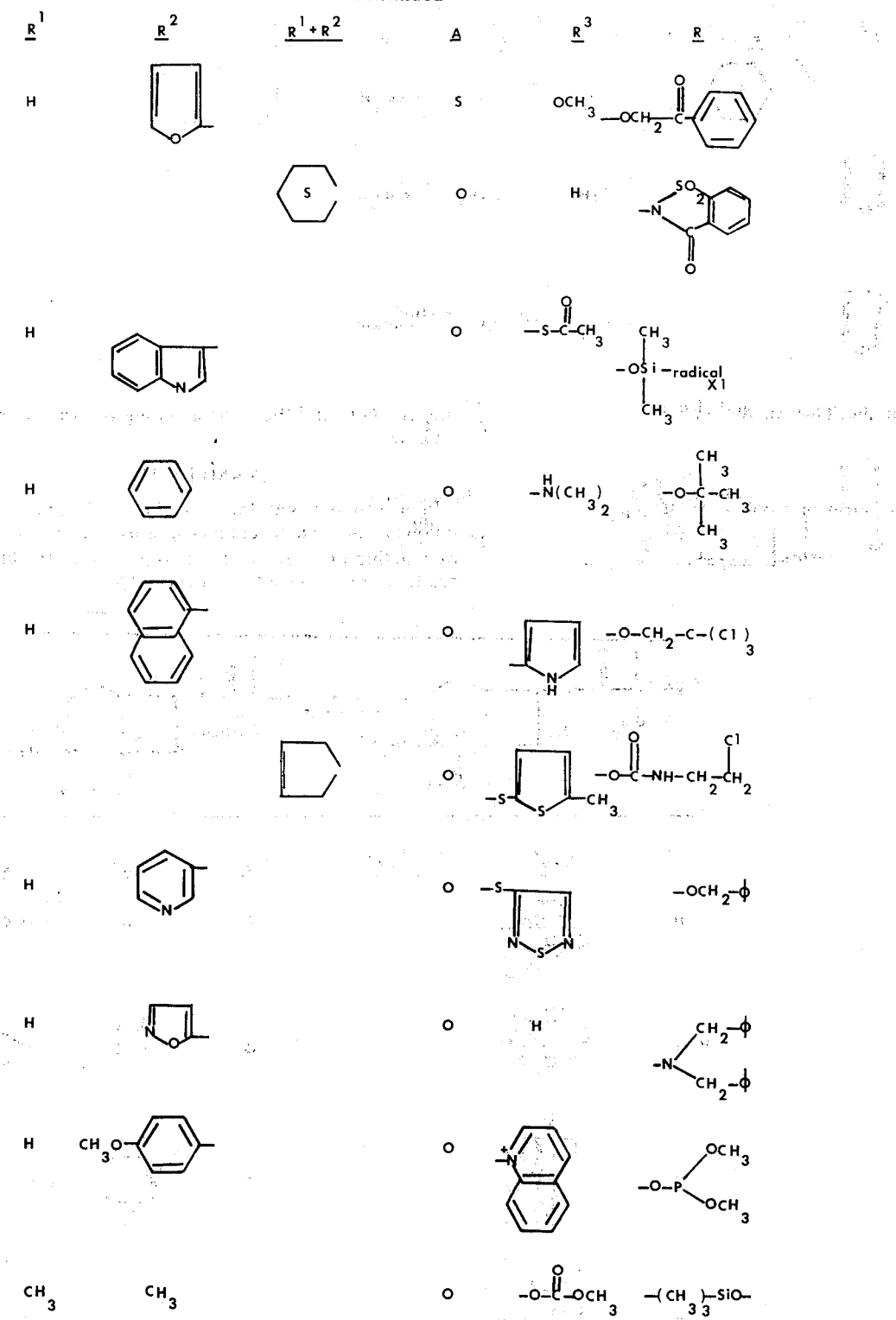
-continued
In this example, radical XI stands for:
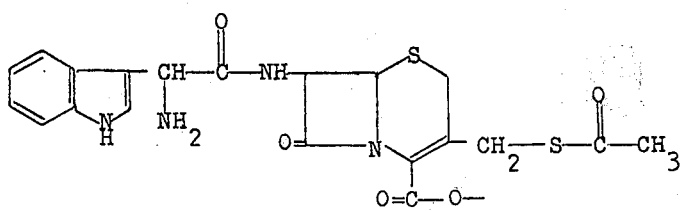

in formula E and the corresponding isocyanate in formula F.

EXAMPLE 12

In accordance with the procedure of Example 1, the following isocyanato cephalosporins can be obtained by selection of the appropriate α-amino substituted starting material of formula G. The compounds of formula G may be prepared in accordance with the procedures described in U.S. application Ser. No. 197,142, now U.S. Pat. No. 3,859,298, the disclosure of which is incorporated herein by reference.

give 4.17 g. product (79%) of the above titled product. An analytical sample is prepared by addition of 1.37 g. of the above titled product in an alcohol-ether solution (15 ml.; 50 ml.) and treatment with an equivalent amount of cyclohexylamine to give 1.0 g. of oil (overall yield, 50%) of the cyclohexylamine salt of the above titled product.

Anal. Calcd. for $C_{24}H_{25}N_5O_5S$. $C_6H_{13}N.H_2O$: C, 58.81; H, 6.58; N, 13.72. Found: C, 59.08; H, 6.61; N, 13.54.

EXAMPLE 14

6-[1-(3-phenylureido)cyclohexanecarboxamido]-penicillanic acid, hemihydrate

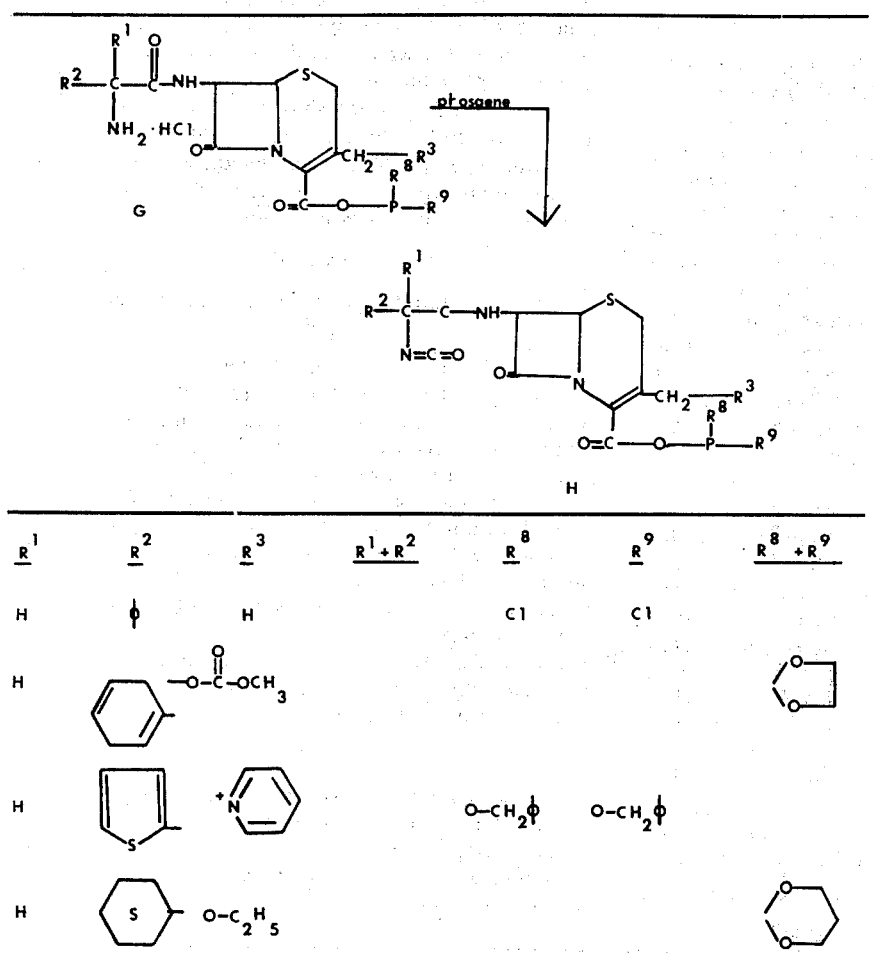

The following examples are illustrative of the use of the isocyanate compounds of the present invention to prepare known as well as novel penicillins or cephalosporins having antibacterial activity.

EXAMPLE 13

6-[D-2-(3-benzimidazolylureido)-2-(1,4-cyclohexadien-1-yl)acetamido]penicillanic acid To a suspension of benzimidazole (1.26 g.; 0.0107 mole) in toluene (50 ml.) with pyridine (2 drops), a solution of the titled compound prepared in Example 1 (4.0 g.; 0.0089 mole) in toluene (15 ml.) is added over 10 min. at 35°C. under nitrogen. After 20 minutes, the reaction mixture is cooled in an ice-bath and moist air is passed through for 2 hrs. The precipitate is collected, washed with toluene and petroleum ether and dried to To a solution of aniline (1.10 ml.; 0.012 mole) and pyridine (2 drops) in toluene (50 ml.), a solution of the trimethylsilyl ester of 6-(1-isocyanatocyclohexanecarboxamido)penicillanic acid (4.40 g.; 0.010 mole) in toluene (15 ml.) is added over 10 min. at 35°C. under nitrogen. After 5 min., the reaction mixture is cooled in an ice-bath, and moist air is passed through for 2 hr. The precipitate is collected, washed with toluene and petroleum ether and dried. The product is dispersed in water, and the mixture is extracted with ethyl acetate. The organic extract is washed with water, brine, and dried over sodium sulfate for 1 hr. and concentrated in vacuo to give a 50% yield of the hemihydrate of the above titled product.

Anal. Calcd. for $C_{22}H_{28}N_4O_5S$. ¼ $H_2O$: C, 56.30; H, 6.23; N, 11.95. Found: C, 56.29; H, 6.43; N, 11.45.

EXAMPLE 15

6-[D-2-(1,4-cyclohexadien-1-yl)-2-ethoxycarbonylaminoacetamido]penicillanic acid To 4.50 g. (0.010 mole) of the titled product of Example 1 is added ethanol (10 ml.) and pyridine (0.1 ml.) at 0°C. The reaction mixture is stirred for 1 hr. at room temperature and then diluted with ether (100 ml.) and extracted with 1 M. phosphate buffer (pH 7.0). The buffer extract is acidified to pH 2.5 and extracted with ethyl acetate. The organic extract is washed with water, brine and dried over sodium sulfate. The solution of the product is concentrated to dryness to give the above titled product.

EXAMPLE 16

6-[D-2-(3-[L-1-carboxy-3-methylthiopropyl]ureido)-2-(1,4-cyclohexadien-1-yl)-acetamido]penicillanic acid A mixture of L-methionine (29.8 g; 0.20 mole) and hexamethyldisilizane (64.4 g; 0.40 mole) is refluxed under nitrogen for 3 hr. to obtain complete solubilization. The reaction is cooled to room temperature and n-hexane (100 ml), triethylamine (10.1 g; 0.10 mole) and trimethylsilyl chloride (10.8 g; 0.10 mole) are added. The reaction is stirred overnight; the precipitated triethylamine hydrochloride is removed by filtration. The filtrate is fractionally distilled at atmospheric pressure to remove the n-hexane and under vacuum to obtain the product N-trimethylsilyl-L-methionine trimethylsilyl ester (43.6 g; 75% yield).

Anal. Calcd. for $C_{11}H_{27}NO_2Si_2S$: C, 45.00; H, 9.26; N, 4.76. Found: C, 44.52; H, 9.42; N, 5.18.

N-trimethylsilyl-L-methionine trimethylsilylester (5.86 g; 0.02 mole), pyridine (0.1 ml), and triethylamine (0.1 ml) are added to a solution of dihydroampicillin isocyanate (8.74 g; 0.02 mole) in chloroform (100 ml). The reaction is stirred overnight and concentrated in vacuo. The residue is taken up in a mixture of ethyl acetate (100 ml) and water (50 ml), and the pH is adjusted to 2.0 with dilute hydrochloric acid. The mixture is stirred for 1 hr, and the ethyl acetate layer is separated, washed with water (50 ml) and brine (2 × 50 ml) and dried with sodium sulfate. The ethyl acetate solution is concentrated in vacuo. The residue is triturated with ether and dried in vacuo to give the above-titled product (7 g; 65% yield).

Anal. Calcd. for $C_{22}H_{30}N_4O_7S_2$: C, 50.17; H, 5.74; N, 10.63. Found: C, 50.39; H, 5.96; N, 10.10.

EXAMPLE 17

6-[D-2-(2-aminoacetamido)-2-(1,4-cyclohexadien-1-yl)acetamido]penicillanic acid 4.48 g. of the isocyanate prepared in Example 1 (0.010 mole) in toluene under dry nitrogen, carbobenzoxyglycine (0.010 mole) and pyridine (0.2 ml.) are added. The reaction is allowed to react until the evolution of carbon dioxide ceases. The reaction mixture is cooled in an ice-bath and cold acetone with 3% water is added. The reaction mixture is diluted with more toluene and extracted with aqueous sodium bicarbonate solution to give a neutral aqueous phase. Upon concentration, the sodium salt is recovered. A 5% solution of this salt in water is added to an aqueous suspension of 30% palladium-barium carbonate (2 × the amount of salt) previously shaken under hydrogen for 1 hr., the mixture is hydrogenated at 15 lbs. pressure for 1 hr., then filtered. The filtrate is adjusted to pH 2.0, then washed with ether. The aqueous phase is adjusted to pH 4.7 and concentrated to give the final product.

EXAMPLE 18

6-(D-2-acetamido-2-phenylacetamido)penicillanic acid

To a solution of the isocyanate derivative of Example 2 (5.1 g.; 11.4 mM) in toluene (50 ml.), acetic acid (0.65 ml.; 11.4 mM) and pyridine (0.2 ml.) are added. After 6 hr., ethyl acetate is added, and the solution is poured over a mixture of ice and water (50 ml.) The pH is adjusted from 6.5 to 2.5, and the mixture extracted with methyl isobutyl ketone. The organic phase is washed with water and brine and dried over sodium sulfate. Cyclohexylamine (1.31 ml.; 11.4 mM) dissolved in a small amount of methyl isobutyl ketone is added dropwise. The initial precipitate that formed is discarded, and the filtrate is concentrated to yield the monohydrated cyclohexylamine salt of the product (1.1 g.; 2.2 mM; 19% yield).

EXAMPLE 19

The isocyanates of the present invention may be reacted with other active hydrogen containing compounds, Grignard reagents or carbanions to produce penicillins having antibacterial activity as illustrated herein.

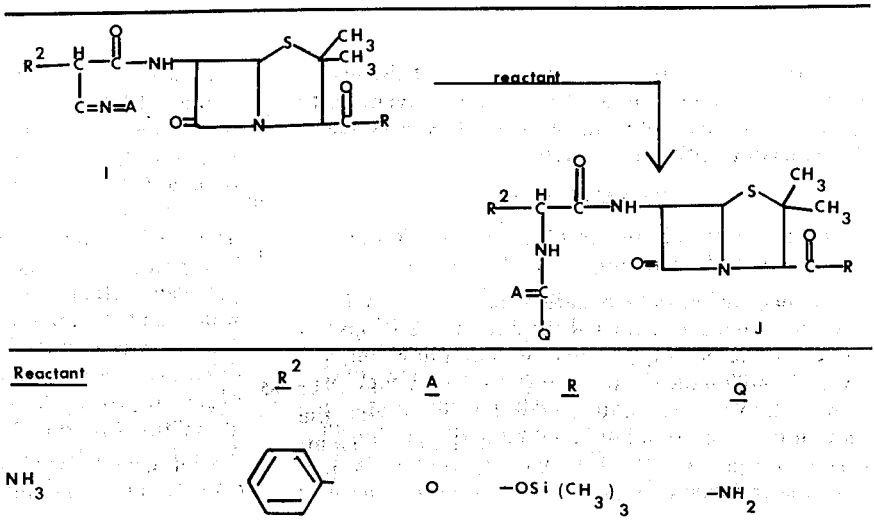

-continued

| Reactant | R² | A | R | Q |
|---|---|---|---|---|
| NH₂CH₃ | thiophene | O | —ONa | —N(H)—CH₃ |
| NH₃ | phenyl | O | —ON(C₂H₅)₃ | —NH₂ |
| CH₃CH₂OH | phenyl | O | —ON(CH₂φ)₂ | O—CH₂CH₃ |
| φ—CH₂CO₂H | thiophene | S | —ONa | —CH₂—φ |
| C₂H₅SO₂NHNH₂ | phenyl | S | —O—P(O—)₂ (cyclic phosphite) | —NHNH—SO₂C₂H₅ |
| C₂H₅NHNH₂ | thiophene | O | —OSi(CH₃)₃ | —NHNH—C₂H₅ |
| φ—NH—C(O)—CH₂—N(H)—OH | phenyl | O | saccharin-N-sulfonyl | —N(OH)—CH₂—C(O)—NH—φ |
| CH₃—CH(—)—CO₂—Si(CH₃)₃ | phenyl | O | —OCH₂—C₆H₄—NO₂ | CH₃—CH(—)—COOH |
| C₂H₅SH | phenyl | O | —ONa | —S—C₂H₅ |
| φ—CH₂—MgX Grignard | NO₂—phenyl | O | — | —CH₂—φ |
| NH₂—C(=NH)—CH₃ | thiophene | O | pyridinium | —N(H)—C(=NH)—CH₃ |

Other known penicillins and cephalosporins within the scope of formulas V and VI may be prepared from the isocyanates of the present invention, including those exemplified in U.S. Pat. Nos. 3,152,050; 3,268,514; 3,340,252; 3,433,784; 3,352,858; 3,471,474; 3,479,339; 3,481,922; 3,483,188; 3,553,202; 3,579,501; 3,579,780; 3,647,780; British Pat. No. 1,250,611; British Pat. No. 1,061,335; British Pat. No. 1,051,675; Belgium Pat. No. 753,387; Belgium Pat. No. 767,647; Belgium Pat. No. 747,382; Belgium Pat. No. 870,531; South African Pat. No. 67/1498; West German Pat. No. 2,055,337; West German Pat. No. 2,127;178; West German Pat. No. 2,127,179; Netherlands Pat. No. 6,610,055; Netherlands Pat. No. 7,005,519; and U.S. Pat. No. 3,673,183.

The compounds of Formulae V & VI in addition to being advantageously utilizable in their acid form, may also be used in the form of the therapeutically-active, non-toxic, pharmaceutically acceptable salts, including acid addition salts at an amino group, e.g. the hydrochloride, sulfate, citrate, succinate, fumarate, maleate, and the like; or non-toxic metallic salts at the carboxy group, such as alkali or alkaline earth metal, e.g. sodium, potassium, calcium and aluminum salts; and as organic salts, e.g., the ammonium salt and substituted ammonium salts, e.g. salts of such non-toxic amines as trialkylamines, e.g. triethylamine, procaine, dibenzylamine, N-benzyl-β-phenethylamine; N, N-alkylene diamines, such as N,N'-dibenzylethylenediamine; N-(lower)alkylpiperidine, e.g. N-ethyl-piperidine; dehydroabietylamine; N,N'-bisdehydroabiethylethylenediamine; and other amines which have been used to form salts with benzyl-penicillin, phenoxymethyl penicillin and the like. Preparation of the desired products in the form of the above-described salts can be accomplished by conventional procedures. For example, the alkali or alkaline earth metal salts can be produced by treatment with an alkaline or alkali earth metal salt of a weak acid, such as 2-ethylhexanoic acid.

When the non-toxic penicillin or cephalosporin compounds prepared from the isocyanates of formula I are employed pharmaceutically, i.e. as antibacterial agents, they may be administered to a host afflicted with a bacterial infection alone or in combination with pharmaceutically acceptable carriers, the proportion of which is determined by the solubility and chemical nature of the compound, chosen route of administration and standard pharmacological practice. For example they may be administered orally in the form of tablets or capsules containing such excipients as starch, milk, sugar, and so forth. They may be administered orally in the form of solution or they may be injected parenterally, e.g. intramuscularly. For parenteral administration, they may be used in the form of a sterile solution or suspensions containing other solutes, for example, enough saline or glucose to make the solution isotonic.

The dosage of the present pharmacologically active agents will vary with the form of administration and the particular compound chosen. Furthermore, it will vary with the particular subject under treatment. Generally, treatment is initiated with small dosages substantially less than the optimum dose of the compound. Thereafter, the dosage is increased by small increments until the optimum effect under the circumstances is reached. It will generally be found that when the composition is administered orally, larger quantities of the active agent will be required to produce the same effect as a smaller quantity given parenterally. In general, the compounds of this invention are most desirably administered at a concentration level that will generally afford effective results without causing any harmful or deleterious side effects.

When the compounds are used in vitro applications, such as disinfecting compositions, they may be dissolved or suspended in a suitable inert carrier, such as water, at a concentration of about 0.1 to 1% by weight and applied by washing or spraying.

The in vitro antibacterial activity of the compounds of Formulae V and VI may be determined by the agar plate dilution method as follows:

A stock solution of the test compound at 10,000 g./ml. is prepared. Two-fold dilutions are made with sterile water, and 1 ml. quanties of dilution are incorporated in 9 ml. of seed agar in sterile petri dishes. Hardened surfaces are inoculated with test organisms and incubated 18 hours at 35°C. The activity of the test compound is measured as the minimal inhibitory concentration (MIC) expressed in g./ml., defined as the least amount of material that completely inhibits the test organism. This test is described in general on pages 303–305 in the "Manual of Clinical Microbiology," J. E. Blair et al., editor, published by the American Society for Microbiology.

The in vivo antibacterial potency of the compounds of Formulae V and VI may be determined as follows:

Mice are divided into four groups of 10 mice in each group. The mice are injected intraperitoneally with 0.5 ml. of a standardized suspension of the infective agent in 5% gastric mucin. Six hours post injection each group of mice receives a single, graded dose of the test compound by the suscutaneous or oral route. All animals are observed for 14 days and deaths are recorded daily. The $CD_{50}$ (curative dose) values are determined by the method of Reed and Muench, American J. of Hygiene, 27, 493 (1938).

What is claimed is:

1. A compound selected from the group having the formula:

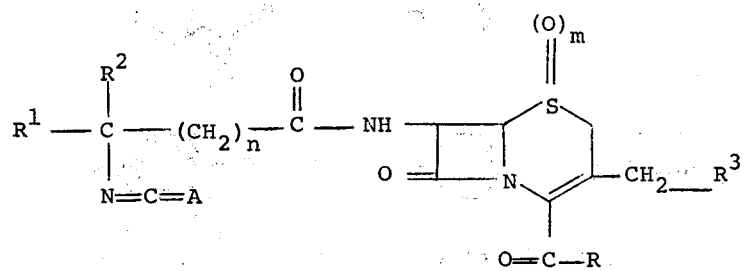

wherein
R¹ is selected from the group consisting of phenyl, substituted phenyl, naphthyl, substituted naphthyl, wherein the substituted phenyl and substituted naphthyl is substituted with a group selected from the class consisting of nitro, halogen, trifluoromethyl, (lower)alkoxy, (lower) alkyl, amino, hydroxy, sulfamyl, di(lower)alkylamino and (lower) alkanoylamino, a cycloalkyl, having from four to eight ring atoms, cycloalkenyl having from four to eight ring atoms and an alicyclic group having from six to eight carbon atoms and containing two or three conjugated or non-conjugated double bonds, a heterocyclic radical selected from the class consisting of thienyl, furyl, pyridyl and pyrimidinyl, R² is hydrogen or lower alkyl having from one to six carbon atoms R³ is selected from the class consisting of hydrogen, pyridinium and an alkanoyloxy radical derived from a hydrocarbon carboxylic acid having from one to eight carbon atoms;

A is sulfur or oxygen;
R is

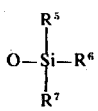

wherein R⁵, R⁶ and R⁷ are selected from the group consisting of lower alkyl, aryl(lower)alkyl, wherein the aryl portion is phenyl or naphthyl, cycloalkyl of 5 to 8 carbon atoms, phenyl and naphthyl;
m is either 0 or 1, n is a whole number from 0 to 3.

2. A compound according to claim 1 wherein R¹ is substituted phenyl or phenyl, R² is hydrogen, R³ is

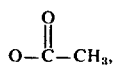

A is oxygen, R is

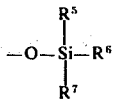

wherein
R⁵, R⁶, R⁷ are lower alkyl
n is a whole number from 0 to 3 and
m is 0.

3. A compound according to claim 2 wherein R¹ is phenyl, R⁵, R⁶ and R⁷ are methyl and n is 0.

4. A compound selected from the group having the formula:

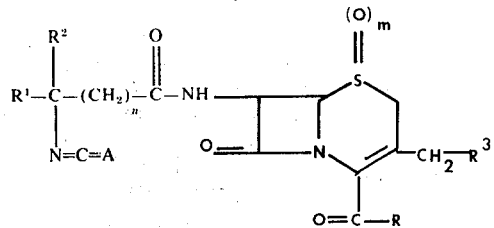

wherein
R¹ is selected from the group consisting of phenyl, substituted phenyl, naphthyl, substituted naphthyl, wherein the substituted phenyl and substituted naphthyl is substituted with a group selected from the class consisting of nitro, halogen, trifluoromethyl, (lower)alkoxy, (lower) alkyl, amino, hydroxy, sulfamyl, di(lower)alkylamino and (lower) alkanoylamino, a cycloalkyl, having from four to eight ring atoms, cycloalkenyl having from four to eight ring atoms and an alicyclic group having from six to eight carbon atoms and containing two or three conjugated or non-conjugated double bonds, a heterocyclic radical selected from the class consisting of thienyl, furyl, pyridyl and pyrimidinyl,
R² is hydrogen or lower alkyl having from one to six carbon atoms
R³ is selected from the class consisting of hydrogen, pyridinium and an alkanoyloxy radical derived from a hydrocarbon carboxylic acid having from one to eight carbon atoms;
A is sulfur or oxygen;
R is selected from the class consisting of

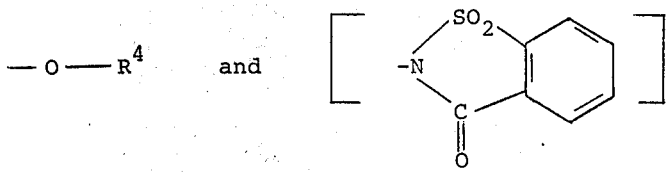

wherein R⁴ is selected from the class consisting of phenyl or naphthyl (lower) alkylene, halo(lower)alkyl, wherein the (lower)alkyl portion has from one to six atoms, phenyl, naphthyl, diphenylmethylene, benzoyl, tert-butyl, phthalimido (lower)alkylene, succinimido(lower)alkylene, C₅ to C₇ tert-alkenyl, C₅ to C₇ tert-alkynyl or a member selected from the group consisting of

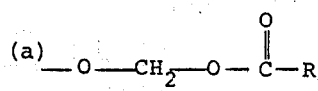

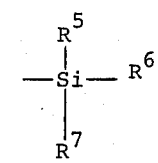

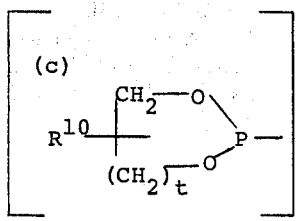

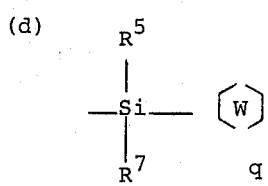

(e) 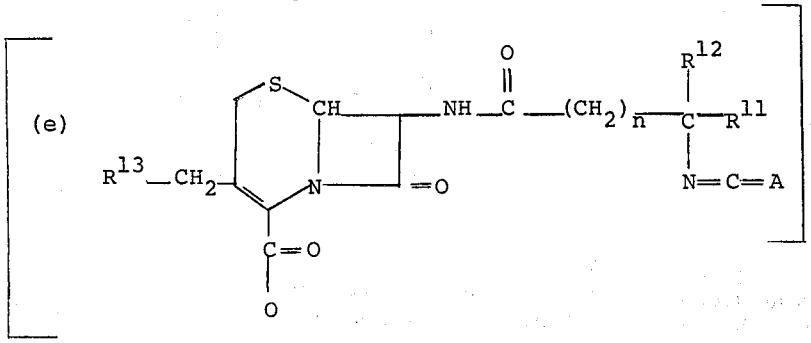

wherein: $R^5$, $R^6$ and $R^7$ are selected from the class consisting of (lower)alkyl and aryl(lower)alkyl; wherein aryl is phenyl or naphthyl W is selected from the group represented by the following formula:

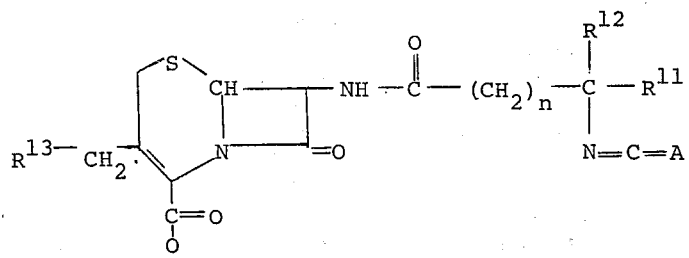

wherein $q$ is a number which is either zero or one, $n$ is a number from 0 through 3, $R^{11}$ is selected from the group consisting of phenyl, substituted phenyl, naphthyl, substituted naphthyl, wherein the substituted phenyl and substituted naphthyl is substituted with a group selected from the class consisting of nitro, halogen, trifluoromethyl, (lower) alkoxy, (lower) alkyl, amino, hydroxy, sulfamyl, di(lower) alkylamino and (lower) alkanoylamino, a cycloalkyl, having from four to eight ring atoms, cycloalkenyl having from four to eight ring atoms and an alicyclic group having from six to eight carbon atoms and containing two or three conjugated or non-conjugated double bonds, heterocyclic radical selected from the class consisting of thienyl, furyl, pyridyl and pyrimidinyl, $R^{12}$ is hydrogen or lower alkyl having from one to six carbon atoms $R^{13}$ is selected from the class consisting of hydrogen, pyridinium and an alkanoyloxy radical derived from a hydrocarbon carboxylic acid having up to eight carbon atoms.

5. A compound according to claim 4 wherein $R^4$ is selected from the class consisting of trimethylsilyl, 1,3,2-dioxaphospholanyl, tert-butyl, benzyl, phthalimidomethyl, succinimidomethyl, pivaloyloxymethyl 2,2,2-phthalimidomethyl, succinimidomethyl, pivaloyloxymethyl, 2,2,2-trichloroethyl, trityl, phenacyl and benzhydryl.

6. A compound according to claim 4 where $R^{11}$ is cycloalkenyl.

7. A compound according to claim 4 wherein $R^{11}$ is cycloalkyl.

8. A compound according to claim 4 wherein $R^{11}$ is an alicyclic group.

9. A compound according to claim 4 wherein R is —O—$R^4$ and $R^4$ is

10. A compound according to claim 4 wherein $R^4$ is O-$R^4$ and $R^4$ is

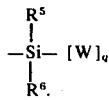

11. A compound according to claim 6, wherein cycloalkenyl is cyclohexenyl.

12. A compound according to claim 4 wherein $R^1$ is phenyl.

13. A compound according to claim 7 wherein cycloalkyl is cyclohexyl.

14. A compound according to claim 8 wherein said alicyclic radical is 1,4 -cyclohexadienyl.

15. A compound according to claim 4 where $R^{11}$ is thienyl.

16. A compound according to claim 4 wherein R is O—$R^4$ and $R^4$ is selected from the class consisting of tert-butyl, benzyl, phenacyl, benzhydryl, trityl, pivaloyloxymethyl, succinimidomethyl and phthalimidomethyl.

17. A compound according to claim 4 which is 7-(D-2-)1, 4-cyclohexadien-1-yl)-2-isocyanatoacetamido)-cephalosporanic acid.

18. A compound according to claim 4 which is 7-(D-2-isocyanato-2-phenylacetamido)cephalosporanic acid, trimethyl silyl ester.

* * * * *